US012751760B2

(12) United States Patent
Lu et al.

(10) Patent No.: US 12,751,760 B2
(45) Date of Patent: Oct. 6, 2026

(54) SMOKE EVACUATION TUBE AND TELESCOPIC SMOKE EVACUATION SCALPEL

(71) Applicant: ZHEJIANG SHUYOU SURGICAL INSTRUMENT CO., LTD., Huzhou (CN)

(72) Inventors: Kongpei Lu, Huzhou (CN); Zuokai Yin, Huzhou (CN)

(73) Assignee: ZHEJIANG SHUYOU SURGICAL INSTRUMENT CO., LTD., Huzhou (CN)

(*) Notice: Subject to any disclaimer, the term of this patent is extended or adjusted under 35 U.S.C. 154(b) by 306 days.

(21) Appl. No.: 18/502,041

(22) Filed: Nov. 5, 2023

(65) Prior Publication Data

US 2024/0074808 A1 Mar. 7, 2024

Related U.S. Application Data

(63) Continuation of application No. PCT/CN2021/096579, filed on May 28, 2021.

(51) Int. Cl.
*A61B 18/14* (2006.01)
*A61B 17/00* (2006.01)
*A61B 18/00* (2006.01)

(52) U.S. Cl.
CPC .................... *A61B 18/1402* (2013.01); *A61B 2017/00477* (2013.01); *A61B 2017/00991* (2013.01); *A61B 2018/00172* (2013.01); *A61B 2018/00196* (2013.01); *A61B 2018/00607* (2013.01); *A61B 2018/1412* (2013.01); *A61B 2218/008* (2013.01)

(58) Field of Classification Search
CPC .......... A61B 18/1402; A61B 2218/008; A61B 2017/00991; A61B 2018/00196
See application file for complete search history.

(56) References Cited

U.S. PATENT DOCUMENTS 5,693,044 A * 12/1997 Cosmescu ............ A61B 18/042 606/49
2015/0209100 A1* 7/2015 Ineson ............... A61B 18/1402 606/42

(Continued)

FOREIGN PATENT DOCUMENTS

CN 111920514 A 11/2020
CN 111920515 A 11/2020
CN 212281616 U 1/2021

*Primary Examiner* — Sean W Collins
(74) *Attorney, Agent, or Firm* — JEEN IP LAW, LLC

(57) ABSTRACT

This patent relates to a smoke evacuation tube and a telescopic smoke evacuation scalpel comprising the smoke evacuation tube. The smoke evacuation tube, comprises a first sleeve (6) and a second sleeve (26). An electrode (8) is mounted inside the first sleeve front section (61), and one end of the electrode (8) protrudes from one end of the first sleeve front section (61); the diameter of the first sleeve (6) is greater than the diameter of the second sleeve (26); a engaging structure used for assembling a lower conductive piece (7) is provided on or outside the second sleeve (26) and inside the first sleeve (6). The telescopic smoke evacuation scalpel comprises an upper conductive piece (10), which is embedded on the pencil body (4); the end of the first sleeve rear section (62) distant from the first sleeve front section (61) is provided with a connection hole.

3 Claims, 7 Drawing Sheets

(56) References Cited

U.S. PATENT DOCUMENTS

| | | | | |
|---|---|---|---|---|
| 2020/0155231 | A1* | 5/2020 | Greep ................ | A61B 18/1402 |
| 2023/0293225 | A1* | 9/2023 | Choi .................. | A61B 18/1402<br>606/41 |

* cited by examiner

SMOKE EVACUATION TUBE AND TELESCOPIC SMOKE EVACUATION SCALPEL

CROSS-REFERENCE TO RELATED APPLICATIONS

The application claims priority to Chinese patent application PCT/CN2021/096579, filed on May 28, 2021, the entire contents of which are incorporated herein by reference.

TECHNICAL FIELD

The invention relates to the technical field of medical device attachments, in particular to a smoke evacuation tube and a telescopic smoke evacuation scalpel.

BACKGROUND

The smoke evacuation scalpel is a high-frequency electric knife that destroys diseased tissue through electric current. It is not caused by simply heating the electrode or the knife head. When the tissue under one point is in contact with the effective electrode or the temperature of the adjacent tissue or cell rises to denature the protein in the cell, coagulation will occur. This precise surgical effect is determined by waveform, voltage, current, tissue The type of the electrode and the shape and size of the electrode are determined. The smoke evacuation scalpel often produces smoke during the cutting and coagulation process, so the smoke evacuation scalpel is connected with a smoke evacuation tube.

In order to meet the technical use requirements for the smoke evacuation electric knife pen, a smoke evacuation scalpel with a telescopic smoke evacuation scalpel is specially introduced. Adjust the length of the smoke evacuation tube to ensure the smoke evacuation effect.

However, the structure of the existing smoke evacuation tube is complex, the conductive function is unstable, and the telescopic locking structure of the smoke evacuation scalpel is complicated, which affects the production efficiency and use.

SUMMARY

In order to solve the above technical problems, the first object of the present invention is to provide a smoke evacuation tube with stable conductive function.

In order to solve the above technical problems, the second object of the present invention is to provide a smoke evacuation scalpel including the smoke evacuation tube structure, the smoke evacuation tube can be stretched, and the telescopic locking structure is simple, easy to disassemble and assemble, and improve production efficiency.

First purpose of the present invention is achieved by the following technical solution:

A smoke evacuation tube, comprising a first sleeve and a second sleeve; the first sleeve includes a front section of the first sleeve and a rear section of the first sleeve, an electrode is installed inside the front section of the first sleeve, and one end of the electrode protrudes from the At one end of the front section of the first sleeve, the diameter of the first sleeve is larger than that of the second sleeve, and an engaging structure for assembling the lower conductive sheet 7 is provided on the upper part or outside of the second sleeve and inside the first sleeve.

Through the structural design, the present invention can realize the expansion and contraction of the smoke evacuation tube structure, and at the same time improve the stability of the electrode and the conductive sheet structure.

Preferably, the engaging structure includes a locking hole provided on the upper part of the second sleeve and located in the inner cavity of the first sleeve for assembling the lower conductive sheet. The engaging structure of the present invention can improve the stability of the structure of the electrode and the conductive sheet, facilitate disassembly and assembly, and improve production efficiency.

Preferably, the engaging structure includes a clamping plate arranged on the outside of the second sleeve and on the inner wall of the first sleeve for assembling the lower conductive sheet. The engaging structure of the present invention can improve the stability of the structure of the electrode and the conductive sheet, facilitate disassembly and assembly, and improve production efficiency.

Preferably, the lower conductive sheet is provided with conductive branches extending vertically or obliquely toward the central axis of the second sleeve.

Preferably, the second sleeve is provided with a rib connecting the first sleeve and the second sleeve.

The second purpose of the present invention is achieved by the following scheme:

Telescopic smoke evacuation scalpel, including the above-mentioned smoke evacuation tube structure, and also includes buttons, PCB board, front cap, first sleeve, lower conductive sheet, electrode and upper conductive sheet, the rear section of the first sleeve is far away from the front section of the first sleeve One end is provided with a communication hole, one end of the lower conductive sheet is connected to the electrode, and the other end of the lower conductive sheet extends to the outside of the rear section of the first casing along the communication hole and then contacts the upper conductive sheet, and the PCB board is electrically connected to the upper conductive sheet. Connection, the PCB board is provided with a contact corresponding to the button, the PCB board is electrically connected with a connecting line, the front cap can be rotatably installed at the end close to the electrode, the first sleeve passes through the front cap, and the inner wall of the front cap is symmetrically connected There are two arc-shaped locking parts, and a locked part with a gradually changing inner diameter is provided near one end of the electrode and at the locking parts.

The telescopic smoke evacuation scalpel of the present invention includes the above-mentioned smoke evacuation tube, and also includes a button, an upper cover, a PCB board, a pen body, a front cap, a first sleeve, a lower conductive sheet, an electrode and a tail cap, and the pen body is tubular, one end of the first sleeve extends into the inside of the pen body, the first sleeve includes a front section of the first sleeve and a rear section of the first sleeve, the electrode is installed inside the front section of the first sleeve and one end of the electrode protrudes from the One end of the front section of the first casing, the pen body is inlaid with an upper conductive sheet, the rear section of the first casing is far away from the front section of the first casing, and a communication hole is provided at the end of the front section of the first casing, one end of the lower conductive sheet is connected to the electrode, and the other end of the lower conductive sheet Extend out along the communication hole to the outside of the rear section of the first casing and then contact the upper conductive sheet. The tail cap is clamped on the end of the pen body away from the electrode, and an opening is opened on the top of the pen body. The upper cover is installed at the opening. The PCB board is electrically connected with the upper conductive sheet, the PCB board is provided with a contact corresponding to the button, the PCB board is electrically connected with a connecting wire, and the connecting wire protrudes from the tail cap to the outside of the pen body, and the other end of the connecting wire is electrically connected There is a plug, the front cap can be rotatably installed on the end of the pen body close to the electrode, the first sleeve passes through the front cap, and the inner wall of the front cap is symmetrically connected with two arc-shaped locking parts, and the inner wall of the pen body close to the electrode is symmetrical Two locked parts are provided with gradually changing inner diameters, and the two locking parts are located at the two locked parts respectively.

In the telescopic smoke evacuation scalpel of the present invention, the locking member is a locking piece, and the locked member is a notch to be locked.

In the telescopic smoke evacuation scalpel of the present invention, a waterproof silicone pad is installed between the upper cover and the pen body, and the waterproof silicone pad is provided with a through hole for the button to pass through.

In the telescopic smoke evacuation scalpel of the present invention, the end of the lower conductive sheet connected to the electrode is designed with inverted teeth, and the lower conductive sheet is connected to the electrodes on multiple sides, and the end of the lower conductive sheet far away from the electrode is designed with a barb.

In the telescopic smoke evacuation scalpel of the present invention, the space between the front section of the first casing and the rear section of the first casing is filled with UV light-curable glue.

In the telescopic smoke evacuation scalpel of the present invention, the upper conductive sheet is provided with a clamping protrusion.

In the telescopic smoke evacuation scalpel of the present invention, the pen body is provided with an annular protrusion on the outer wall near one end of the front cap, and the inner wall of the front cap is provided with an annular groove matching the annular protrusion.

In the telescopic smoke evacuation scalpel of the present invention, the front cap and the pen body are provided with anti-slip protrusions.

In the telescopic smoke evacuation scalpel of the present invention, there are two buttons, one is a cutting function button, and the other is a coagulation function button.

Compared with prior art, the beneficial effects of the present invention are:

1. Through the structural design of the smoke evacuation tube, the present invention can realize the expansion and contraction of the smoke evacuation tube structure and improve the stability of the structure of the electrode and the conductive sheet.

2. When the smoke evacuation scalpel is in normal use, the waterproof silicone pad improves the sealing of the two buttons, and the tail cap is connected to the input end of the external suction device. Insert the plug into the socket to power on the whole device, and control the two buttons to open For operations such as closing, when it is necessary to adjust the extension length of the first sleeve, rotate the front cap, and under the action of the locked parts with gradually changing inner diameters, the two sets of locking parts rotate from the short diameter of the locked parts to the long At the diameter, the two sets of locking parts are deformed and separated from the first sleeve, and then the front section of the first sleeve is pulled to adjust the position of the first sleeve. After the adjustment, the front cap is reversely rotated, and the two sets of locking parts The long diameter of the locked part moves to the short diameter, and the two sets of locking parts deform and contact the outer wall of the first sleeve to lock the position of the first sleeve. When the first sleeve moves, the lower conductive sheet moves away from the One end of the front cap is always in contact with the upper conductive sheet to maintain a conductive state.

Figure 1:
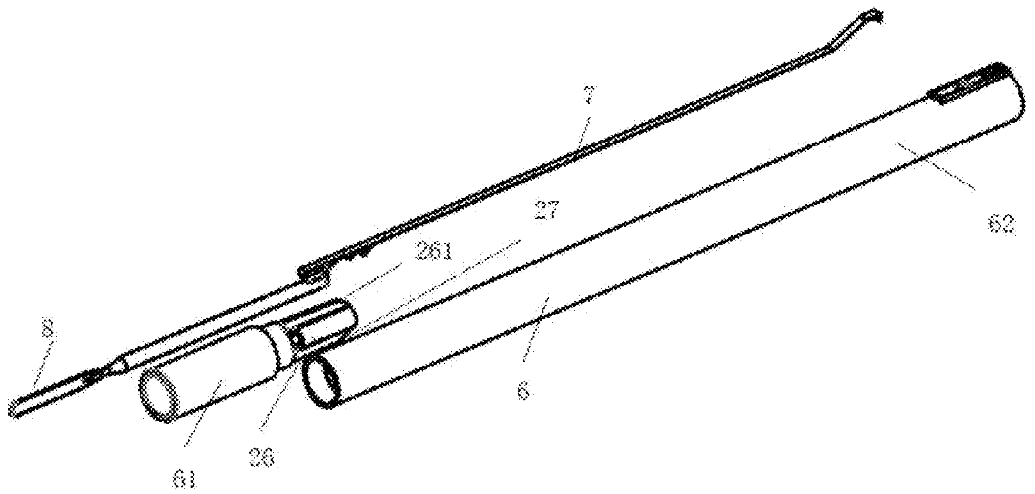
FIG. 1 is the explosion schematic diagram of a kind of structure of smoke evacuation tube of the present invention.

Marks in the drawings: 1. button; 2. upper cover; 3. PCB board; 4. pen body; 5. front cap; 6. first sleeve; 7. lower conductive sheet; 8. electrode; 61. front section of the first casing; 62. rear section of the first casing; 10. upper conductive sheet; 11. connecting wire; 12. arc-shaped locking part; 13. locked part; 14. waterproof silicone pad; 15. inverted teeth; 16. barb; 17. clamping protrusion; 18. annular protrusion; 19. anti-slip protrusion; 26. second sleeve;

DETAILED DESCRIPTION OF THE EMBODIMENTS

The specific implementation manners of the present invention will be further described in detail below in conjunction with the accompanying drawings and embodiments. The following examples are used to illustrate the present invention, but are not intended to limit the scope of the present invention.

As shown in FIGS. 1 to 8, the smoke evacuation tube includes a first sleeve 6 and a second sleeve 26; its first sleeve 6 includes a first sleeve front section 61 and a first sleeve rear section 62, the first sleeve An electrode 8 is installed inside the front section 61 of the tube, and one end of the electrode 8 protrudes from one end of the front section 61 of the first sleeve. An engaging structure for assembling the lower conductive sheet 7 is disposed inside the first sleeve 6. A rib 27 connecting the first sleeve 6 and the second sleeve 26 is disposed on the second sleeve 26.

One structure of the engaging structure may be, as shown in FIG. 1, a locking hole 261 provided on the upper part of the second sleeve 26 and located in the inner cavity of the first sleeve 6 for assembling the lower conductive sheet 7.

Figure 2:
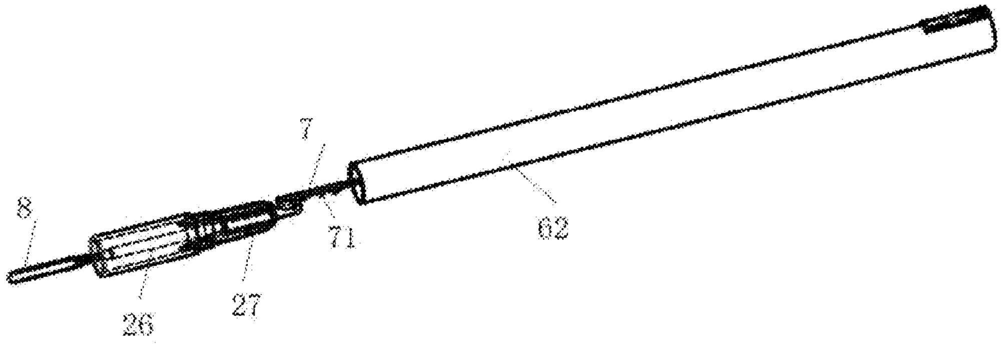
FIG. 2 is the explosion schematic diagram of another structure of the smoke evacuation tube of the present invention.
Figure 3:
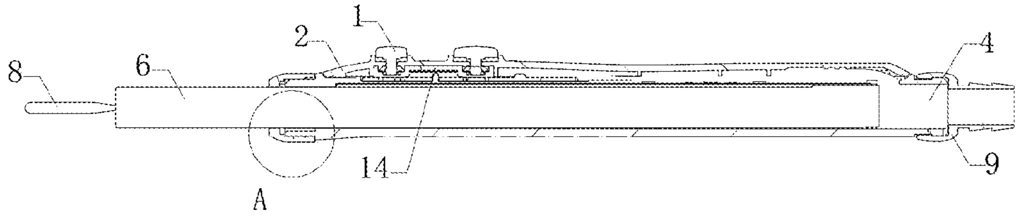
FIG. 3 is a schematic structural view of the telescopic smoke evacuation scalpel of the present invention.
Figure 4:
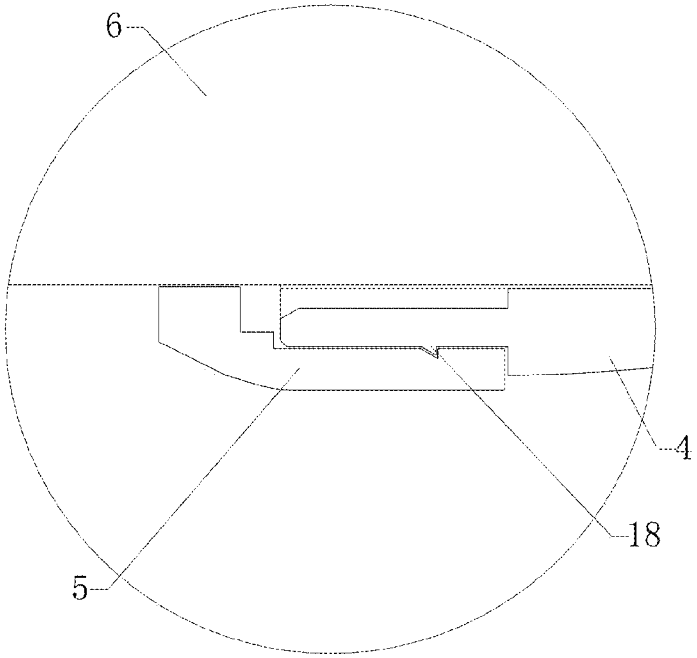
FIG. 4 is a partial enlarged view of part A in FIG. 3.
Figure 5:
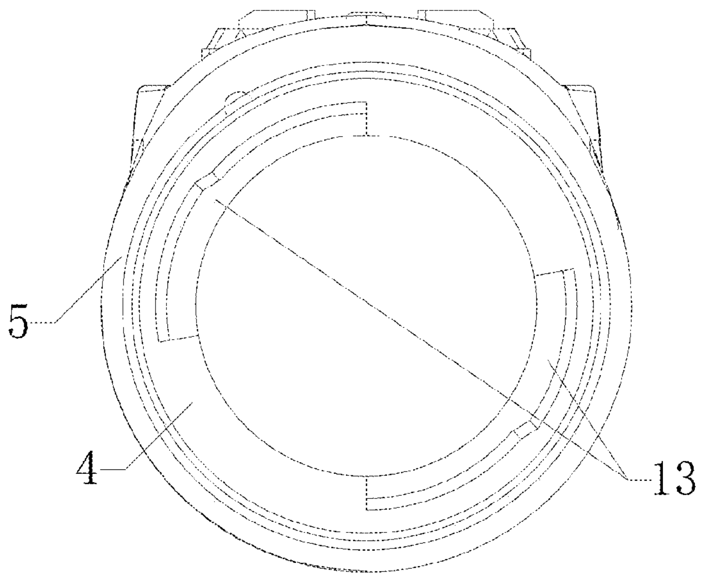
FIG. 5 is a left view of the front cap, the pen body and two groups of locked parts.
Figure 6:
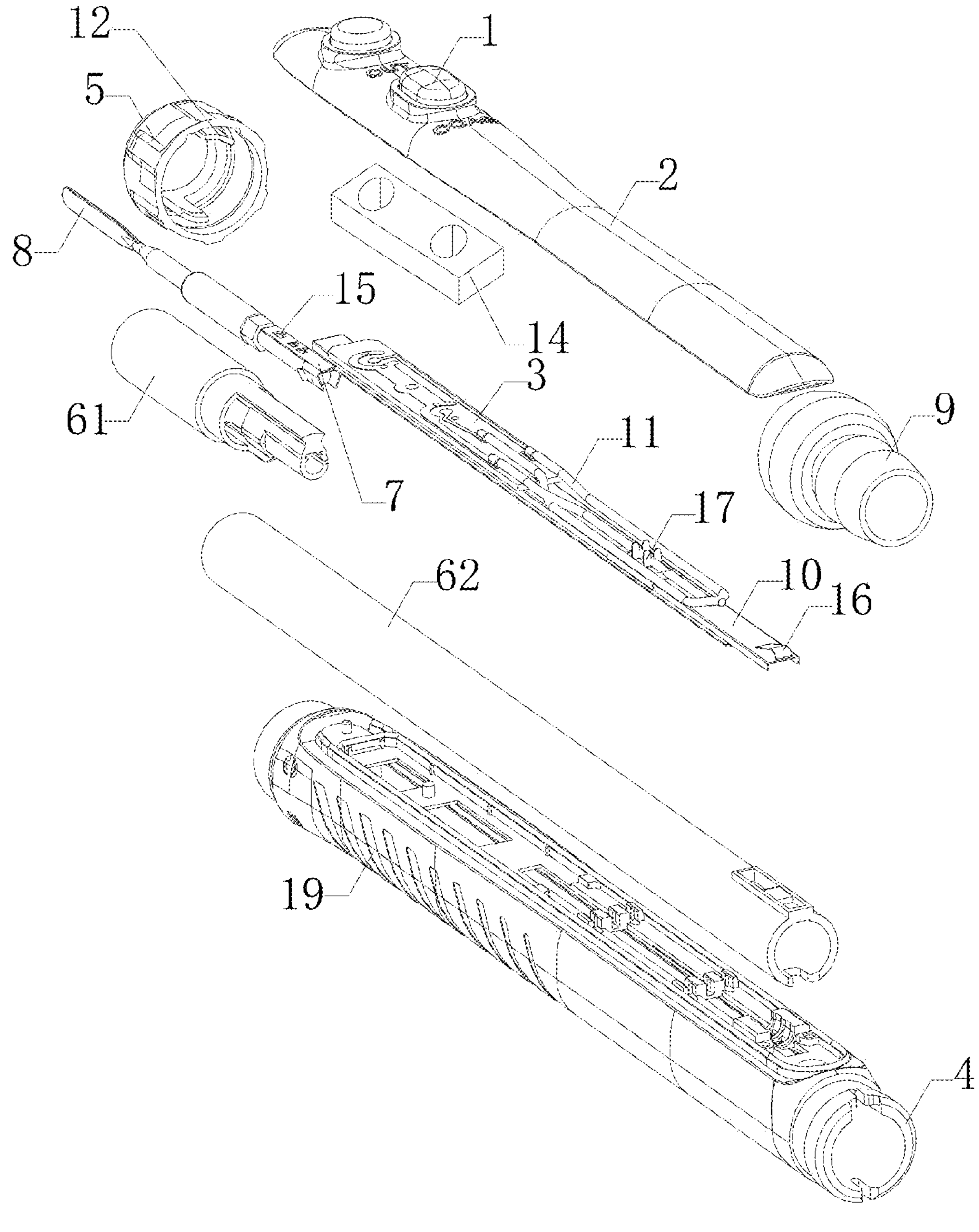
FIG. 6 is an exploded view of the telescopic smoke evacuation scalpel of the present invention.
Figure 7:
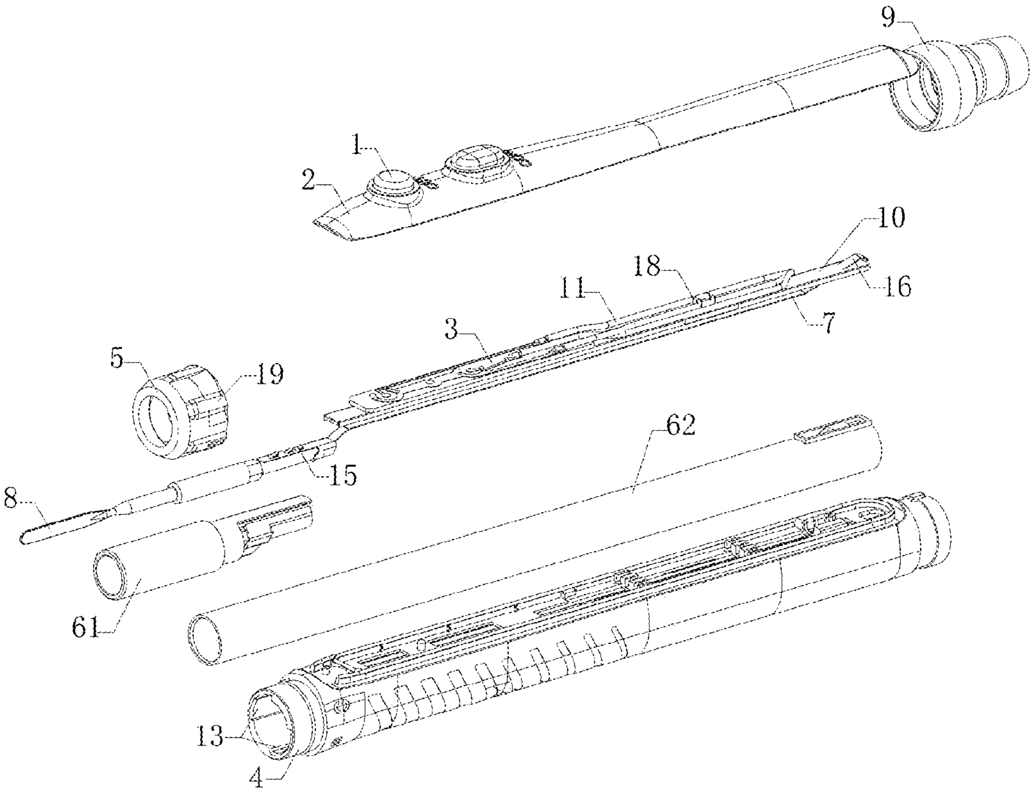
FIG. 7 is an exploded view of the telescopic smoke evacuation scalpel of the present invention.

Another structure of the engaging structure may be, as shown in FIG. 2, a clamping plate provided on the outside of the second sleeve 26 and on the inner wall of the first sleeve 6 for assembling the lower conductive sheet 7. In order to further increase the conductivity, the lower conductive sheet 7 is provided with conductive branches 71 extending vertically or obliquely toward the central axis of the second sleeve 26.

The telescopic smoke evacuation scalpel of the present invention comprises a button 1, an upper cover 2, a PCB board 3, a pen body 4, a front cap 5, a first sleeve 6, a lower conductive sheet 7, an electrode 8 and a tail cap 9, and the pen body 4 is Tubular, one end of the first sleeve 6 extends into the inside of the pen body 4, the first sleeve 6 includes a first sleeve front section 61 and a first sleeve rear section 62, the electrode 8 is installed inside the first sleeve front section 61 and the electrode One end of 8 protrudes from one end of the first sleeve front section 61, the pen body 4 is inlaid with an upper conductive sheet 10, the first sleeve rear section 62 is provided with a communication hole away from the end of the first sleeve front section 61, and one end of the lower conductive sheet 7 is connected to the electrode. 8 connection, the other end of the lower conductive sheet 7 protrudes to the outside of the first sleeve rear section 62 along the communication hole and then contacts the upper conductive sheet 10, the tail cap 9 is clamped on the end of the pen body 4 away from the electrode 8, and the top of the pen body 4 is opened There is an opening, the upper cover 2 is installed in the opening, the PCB board 3 is electrically connected to the upper conductive sheet 10, the contact point corresponding to the button 1 is arranged on the PCB board 3, and the connecting wire 11 is electrically connected to the PCB board 3, the connecting wire 11 protrudes to the outside of the pen body 4 along the tail cap 9, the other end of the connecting wire 11 is electrically connected to a plug, the front cap 5 is rotatably installed on the end of the pen body 4 close to the electrode 8, the first sleeve 6 passes through the front cap 5, and the front cap 5 The inner wall of the cap 5 is symmetrically connected with two arc-shaped locking parts 12, and the inner wall of the pen body 4 near the electrode 8 is symmetrically provided with two locked parts 13 with gradually changing inner diameters. The two locking parts 12 are respectively located at two There are 13 locked parts; during normal use, the tail cap 9 is connected to the input end of the external air suction device, the plug is not drawn and inserted into the socket to power the device as a whole, and the button 1 is controlled to open and close operations. When adjusting the protruding length of the first sleeve 6, the front cap 5 is rotated, and under the action of the two locked parts 13 with gradually changing inner diameters, the two groups of locking parts 12 are rotated from the short diameter of the locked parts 13 to At the long diameter, the two sets of locking parts 12 are deformed and separated from the first sleeve 6, and then the front section 61 of the first sleeve is pulled to adjust the position of the first sleeve 6. After the adjustment, the front cap 5 is reversely rotated, The two groups of locking parts 12 move from the long diameter of the locked part 13 to the short diameter, and the two groups of locking parts 12 deform and contact the outer wall of the first sleeve 6 to lock the position of the first sleeve 6. When the casing 6 moves, the end of the lower conductive sheet 7 away from the front cap 5 is always in contact with the upper conductive sheet 10 to maintain a conductive state.

In the telescopic smoke evacuation scalpel of the present invention, a waterproof silicone pad 14 is installed between the upper cover 2 and the pen body 4, and the waterproof silicone pad 14 is provided with a through hole for the button 1 to pass through; tightness.

In the telescopic smoke evacuation scalpel of the present invention, the end of the lower conductive sheet 7 connected to the electrode 8 is designed with a barb 15, and the lower conductive sheet 7 is connected to the electrode 8 on multiple sides, and the end of the lower conductive sheet 7 away from the electrode 8 is designed with a barb 16; The end connecting the sheet 7 and the electrode 8 is designed with inverted teeth 15 to improve the connection reliability between the lower conductive sheet 7 and the front section 61 of the first sleeve. One end of the electrode 8 is designed with a barb 16 to prevent the lower conductive sheet 7 from falling off when the first sleeve 6 is pulled.

In the telescopic smoke evacuation scalpel of the present invention, the space between the front section 61 of the first casing and the rear section 62 of the first casing is filled with UV light-curable glue; the front section 61 of the first casing and the rear section 62 of the first casing adopt a slot design, Prevent relative rotation, and fill with UV photocurable glue to strengthen the fixation.

In the telescopic smoke evacuation scalpel of the present invention, the upper conductive sheet 10 is provided with a clamping protrusion 17;

In the telescopic smoke evacuation scalpel of the present invention, the outer wall of the pen body 4 near the end of the front cap 5 is provided with an annular protrusion 18, and the inner wall of the front cap 5 is provided with an annular groove that matches the annular protrusion 18; through the annular protrusion 18 and the annular The grooves match, and the front cap 5 is rotatably mounted on the pen body 4.

In the telescopic smoke evacuation scalpel of the present invention, the front cap 5 and the pen body 4 are provided with anti-slip protrusions 19 to increase the friction between the knife and the user.

In the telescopic smoke evacuation scalpel of the present invention, two buttons 1 are provided, one is a cutting function button, and the other is a coagulation function button; cutting is controlled by the cutting function button, and coagulation is controlled by the coagulation function button.

The telescopic smoke evacuation scalpel of the present invention, in normal use, controls cutting through the cutting function button, controls coagulation through the blood coagulation function button, and the waterproof silicone pad 14 improves the sealing performance of the two buttons 1, and the input of the tail cap 9 and the external suction device The end is connected, and the plug (not shown) is inserted into the socket to power on the device as a whole, and the two buttons 1 are controlled to open and close operations. Under the action of the gradually changing two locked parts 13, two groups of locking parts 12 rotate from the short diameter of the locked parts 13 to the long diameter, and the two groups of locking parts 12 are deformed and separated from the first sleeve 6, and then pull the front section 61 of the first sleeve to adjust the position of the first sleeve 6. After the adjustment, reversely rotate the front cap 5, and the two groups of locking parts 12 will move from the long diameter of the locked part 13 to the short diameter, diameter, the two sets of locking parts 12 deform and contact the outer wall of the first sleeve 6, and lock the position of the first sleeve 6. When the first sleeve 6 moves, the end of the lower conductive piece 7 away from the front cup 5 and the upper The conductive sheet 10 is always in contact and remains in a conductive state.

In the telescopic smoke evacuation scalpel of the present invention, the installation, connection or arrangement of all the above-mentioned components are welding, riveting or other common mechanical methods, wherein the sliding/rotating fixing means that the sliding/rotating state does not fall off, and the sealing Communication means that the two connectors are connected and sealed at the same time, and the specific structure, model and coefficient index of all its components are its own technology, as long as it can achieve its beneficial effect, it can be implemented. All the above-mentioned power consumption modules and electrical appliances They are all common electrical components on the market. When buying them back for use, they only need to be electrically connected to each other according to the instruction manual purchased together, and the control module is a common self-contained module, so they will not be repeated here.

For the telescopic smoke evacuation scalpel of the present invention, unless otherwise specified, the orientation words included in the term, such as "up, down, left, right, front, back, inside and outside, and vertical and horizontal", only represent the orientation of the term in the normal use state, or are based on the It is a common term understood by those skilled in the art, and should not be regarded as a limitation of the term. At the same time, the number sequence nouns such as "first", "second" and "third" do not represent specific quantities and orders, but are merely used Moreover, the term "comprises". "comprises" or any other variation thereof is intended to cover a non-exclusive inclusion such that a process, method, article or apparatus comprising a set of elements includes not only those elements but also Including other elements not expressly listed, or also including elements inherent in such process, method, article or apparatus.

The above is only a preferred embodiment of the present invention, it should be pointed out that for those of ordinary skill in the art, without departing from the technical principle of the present invention, some improvements and modifications can also be made, these improvements and modifications It should also be regarded as the protection scope of the present invention.

What is claimed is:

1. A telescopic smoke evacuation scalpel, comprising a smoke evacuation tube, characterized in that, the smoke evacuation tube comprising a first sleeve (6) and a second sleeve (26), the first sleeve (6) includes a first sleeve front section (61) and a first sleeve rear section (62), and an electrode (8) is installed inside the first sleeve front section (61) and one end of the electrode (8) protrudes from one end of the first sleeve front section (61), the diameter of the first sleeve (6) is larger than the diameter of the second sleeve (26), on or outside the second sleeve (26) and located at the first sleeve (6) is provided with an engaging structure for assembling a lower conductive sheet (7);

the lower conductive sheet (7) is provided with conductive branches (71) extending vertically or obliquely toward the central axis of the second sleeve (26);

a rib (27) connecting the first sleeve (6) and the second sleeve (26) is arranged on the second sleeve (26);

the telescopic smoke evacuation scalpel also includes a button (1), an upper cover (2), a PCB board (3), a pen body (4), a front cap (5), a tail cap (9) and an upper conductive sheet (10), and the first sleeve rear section (62) is provided with a communication hole away from the end of the first sleeve front section (61), one end of the lower conductive sheet (7) is connected to the electrode (8), and the other end of the lower conductive sheet (7) extends out along the communication hole to the outside of the rear section of the first sleeve (62) is then in contact with the upper conductive sheet (10), and the PCB board (3) is electrically connected to the upper conductive sheet (10);

the pen body (4) is tubular, one end of the first sleeve (6) extends into the inside of the pen body (4), and the pen body (4) is inlaid with the upper conductive sheet (10), the tail cap (9) is clamped on the end of the pen body (4) away from the electrode (8), the top of the pen body (4) is provided with an opening, the upper cover (2) is installed at the opening, and the PCB board (3) electrically connected with the upper conductive sheet (10), the PCB board (3) is provided with a contact corresponding to the button (1), the PCB board (3) is electrically connected with a connecting wire (11), and the connecting wire (11) extending out to the outside of the pen body (4) along the tail cap (9), other end of the connecting wire (11) is electrically connected to a plug; the front cap (5) is rotatably mounted on the pen body (4) facing the electrode (8) end, the first sleeve (6) passes through the front cap (5), and the inner wall of the front cap (5) is symmetrically connected with two arc-shaped locking parts (12), and inner wall of the pen body (4) at an end adjacent to the electrode (8) is symmetrically provided with two locked parts (13) having an increased inner diameter, and the two arc-shaped locking parts (12) are located at the two locked parts (13) respectively;

the arc-shaped locking parts (12) are locking pieces, the locked parts (13) are notched to be locked;

the lower conductive sheet (7) connected to the electrode (8) is designed with inverted teeth (15), and the lower conductive sheet (7) is connected to the electrode (8) on multiple sides, and the lower conductive sheet (7) away from end of the electrode (8) is designed with barbs (16).

2. The telescopic smoke evacuation scalpel of claim 1, wherein the engaging structure includes a locking hole (261) arranged on upper part of the second sleeve (26) and located in the inner cavity of the first sleeve (6) for assembling the lower conductive sheet (7).

3. The telescopic smoke evacuation scalpel of claim 1, wherein the engaging structure includes a clamping plate arranged outside the second sleeve (26) and on the inner wall of the first sleeve (6) for assembling the lower conductive sheet (7).

* * * * *